United States Patent
Fry et al.

(10) Patent No.: US 8,620,681 B2
(45) Date of Patent: *Dec. 31, 2013

(54) SYSTEM AND METHOD FOR AUTOMATICALLY VERIFYING MULTIPLE LABORATORY TEST RESULTS IN A COMPUTERIZED ENVIRONMENT

(75) Inventors: Jeffrey D. Fry, Lansing, KS (US); Lori N. Cross, Kansas City, MO (US); Arthur J. Hauck, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 423 days.

This patent is subject to a terminal disclaimer.

(21) Appl. No.: 12/818,852

(22) Filed: Jun. 18, 2010

(65) Prior Publication Data
US 2010/0256989 A1 Oct. 7, 2010

Related U.S. Application Data

(63) Continuation of application No. 11/021,878, filed on Dec. 22, 2004, now Pat. No. 7,769,597.

(51) Int. Cl.
*G06Q 50/00* (2012.01)

(52) U.S. Cl.
USPC ................................ 705/2; 705/3; 600/300

(58) Field of Classification Search
USPC .................................................. 705/2–3
See application file for complete search history.

(56) References Cited

U.S. PATENT DOCUMENTS

| 6,018,713 A * | 1/2000 | Coli et al. ............ 705/2 |
| 6,581,012 B1 * | 6/2003 | Aryev et al. .......... 702/22 |
| 2002/0161606 A1 * | 10/2002 | Bennett et al. ........ 705/2 |

* cited by examiner

*Primary Examiner* — Sind Phongsvirajati
(74) *Attorney, Agent, or Firm* — Shook, Hardy & Bacon L.L.P.

(57) ABSTRACT

The present invention relates to a method of holding laboratory test results in a computerized environment. A first laboratory test result is received, and is related to one or more other laboratory tests that comprise a healthcare order. It is determined whether the test results of the order have been received. If they have all been received, the test results are compared to predefined criteria and are determined to be considered normal. Once determined to be considered normal, the order is automatically verified. If the tests results of the healthcare order have not all been received, the first laboratory test result is held until all of the test results have been received.

20 Claims, 3 Drawing Sheets

SYSTEM AND METHOD FOR AUTOMATICALLY VERIFYING MULTIPLE LABORATORY TEST RESULTS IN A COMPUTERIZED ENVIRONMENT

CROSS-REFERENCE TO RELATED APPLICATIONS

This application is a continuation of U.S. Ser. No. 11/021,878, filed on Dec. 22, 2004, the disclosure of which is hereby incorporated by reference.

STATEMENT REGARDING FEDERALLY SPONSORED RESEARCH OR DEVELOPMENT

Not applicable.

TECHNICAL FIELD

The present invention relates generally to the field of computer software. More particularly, the present invention relates to automatically verifying multiple laboratory tests results in a computerized environment.

BACKGROUND OF THE INVENTION

Laboratory tests are ordered by healthcare providers to be performed for a patient in a healthcare environment. Examples of these tests include analyzing fluid or bodily tissue, such as blood or urine. A fluid or tissue sample is taken from a patient and sent to a laboratory to be tested. One or more instruments within the laboratory perform ordered tests on the sample. The instrument performs the test and provides an electronic message of the test results.

The test results are verified using a decision process to determine what is normal or acceptable for a test result for a patient. For example, verification may determine whether the test result is within a predetermined range that is considered to be normal for that type of laboratory test. Previously, a technologist or clinician in the laboratory verified laboratory test results. This process was time consuming and prone to human error.

Other systems have attempted to automate the decision process and verify laboratory test results electronically. The systems evaluate each result individually against predefined decision rules to determine if the result should be released by the system for clinical use. However, these systems are unable to evaluate multiple test results from the same order that are routed from different instruments, testing stations or modular instruments. The laboratory test result messages coming from different instruments may be related to one order. These systems cannot determine if the entire set of laboratory test results satisfies the predefined verification rules prior to releasing the test results. Thus, since laboratory test results can only be evaluated within the context of an individual laboratory test result, some results may be automatically verified even though subsequent related laboratory test results have information that would cause all the results in the set or order to not be automatically verification. Furthermore, these systems cannot automatically verify multiple test results received from multiple areas of modular laboratory instruments.

It would be beneficial to be able to hold laboratory test results from a set or group until all of the laboratory test results for the set or group have been received so that the results as a group may be compared to the predefined auto-verification rules and auto-verified.

SUMMARY OF THE INVENTION

In one embodiment, a method of holding laboratory test results in a computerized environment is recited. The method includes one or more computing devices executing receiving a first laboratory test result for a healthcare order for a patient, wherein the healthcare order comprises multiple laboratory tests that are related to one another. The method further includes determining whether all test results associated with the laboratory tests for the healthcare order have been received. If the test results associated with all of the laboratory tests for the healthcare order have been received, the method includes comparing each of the test results to predefined criteria, determining that each of the test results is considered to be normal, and automatically verifying the entire order. Further, if the test results associated with all of the laboratory tests for the healthcare order have not been received, the method includes holding the first laboratory test result until all of the test results for the healthcare order have been received.

In another embodiment, a system having a computer to perform a method for suspending processing of laboratory test results in a computerized environment is disclosed. The system includes the computer configured to execute a receiving component for receiving a first laboratory test result for a patient, wherein a healthcare order comprises the first laboratory test result and a second laboratory test result. The system also includes a determining component for determining whether all of the laboratory test results for the healthcare order have been received, and a comparing component for comparing each of the test results for the healthcare order to predefined criteria. Additionally, the system includes a suspending component for suspending processing of the first laboratory test result if the second laboratory test result has not been received, and a verifying component for automatically verifying the entire order when all of the test results have been received.

In yet another embodiment, a method is provided for holding laboratory test results in a computerized environment. The method includes one or more computing devices executing receiving a first laboratory test result for a healthcare order for a patient, wherein the healthcare order comprises the first laboratory test result and a second laboratory test result. The method also includes holding the first laboratory test result until the second laboratory test result has been received. Upon receiving the second laboratory test result, the method additionally includes determining that the first laboratory test result is within a predetermined range that is considered to be normal for that type of laboratory test, and determining that the second laboratory test result is within the predetermined range that is considered to be normal for that type of laboratory test. The healthcare order is automatically verified.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

The present invention allows the coordination of laboratory test results from multiple sources and/or interface instruments at one time. It decreases the multitude of individual orders that automatically fail general auto-verification. The present invention provides the ability to automatically verify (auto-verify) results requiring multiple instruments to perform tests for the same order and allows for auto-verification of results received from multiple areas of modular instruments.

Figure 1:
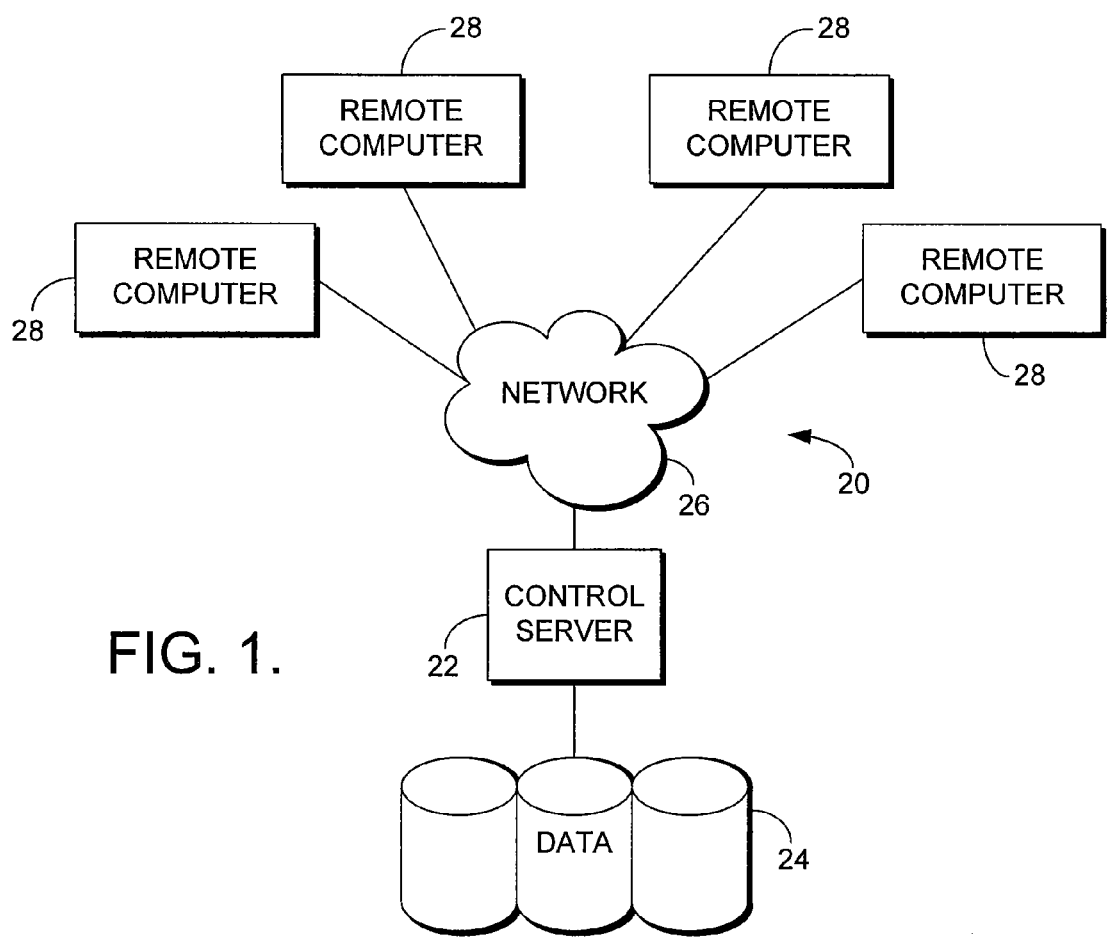
FIG. 1 is a block diagram of a computing system environment suitable for use in implementing the present invention.

With reference to FIG. 1, an exemplary medical information system for implementing the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, laboratory experts, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system operating in conjunction with an Internet-based system, one skilled in the art would recognize that the method and system can be implemented in any system supporting the receipt and processing of laboratory test results.

Figure 2:
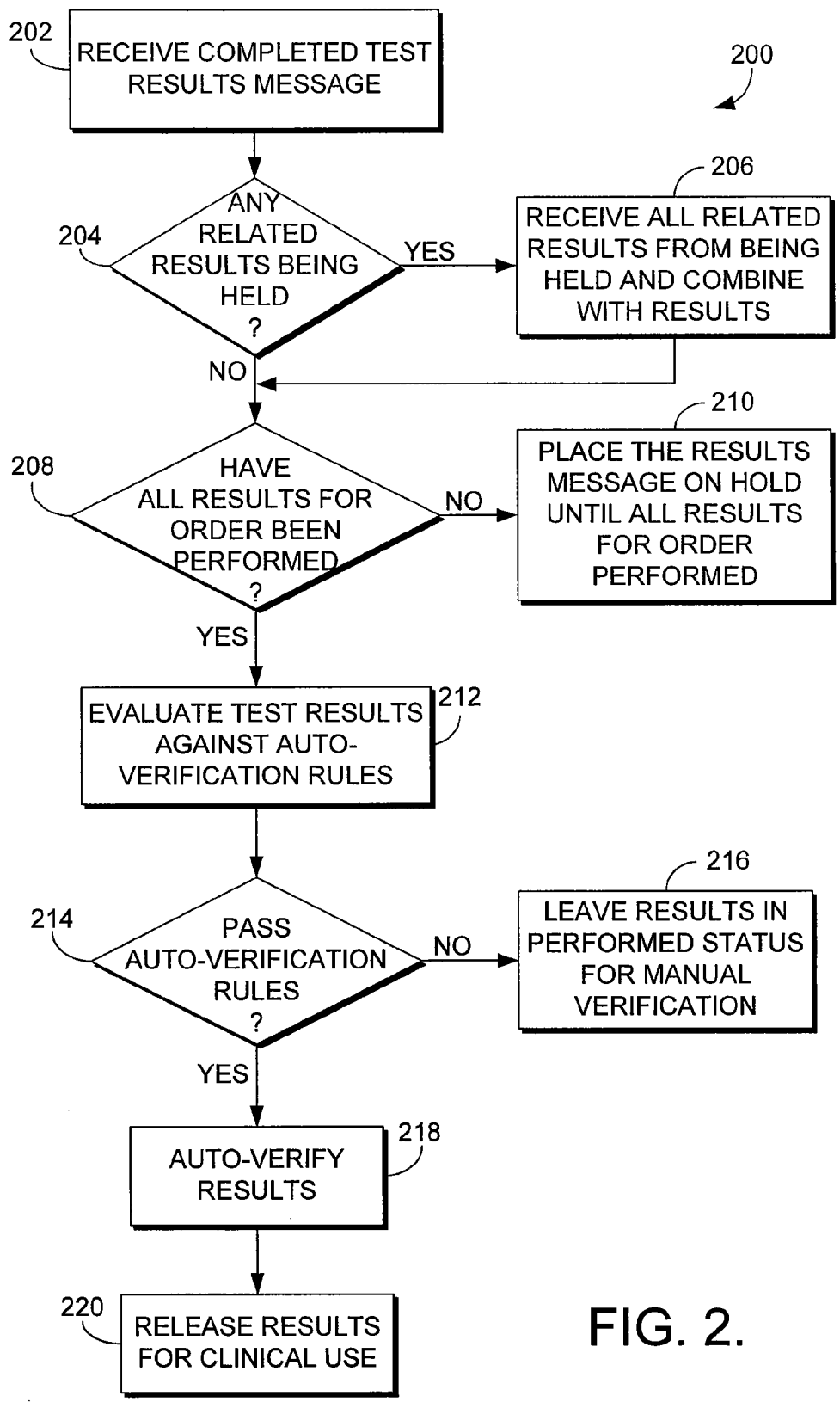
FIG. 2 is a flow diagram of automatically verifying a set of laboratory test results in accordance with an embodiment of the present invention.

With reference to FIG. 2, a method for automatically verifying multiple laboratory test results 200 is shown. At block 202, one or more completed test results from an instrument, result source or testing station in the laboratory are received. In one embodiment, one or more completed laboratory test results are received in the form of an electronic message. At decision block 204 it is determined whether there are any other related results to the laboratory test results received at block 202 being held. For example, it is determined whether any of the laboratory test results from the same order as the result received are being held. A healthcare order may comprise a set of related healthcare tests. For example, an order for a lipid profile comprises a cholesterol test, a triglyceride test and an HDL test. The related tests may be performed on the same or different instruments. Thus, if a result for an HDL test for the patient is received, at block 202, the system determines if the results for the cholesterol and triglyceride tests have been received.

If, at block 204, it is determined there are related results, being held at block 206, laboratory results related to the results received at block 202 are received. The related results are combined with the results received at block 202. Continuing the above example, if the cholesterol and triglyceride tests are being held, they are combined with the HDL test for the patient received at block 202. At decision block 208, it is determined whether all results for the order containing the laboratory test result received at block 202 have been performed and received. The tests may have been performed at multiple, different instruments in the laboratory. The results may also have been performed on multiple areas of modular instruments. The results from tests performed on different instruments may be received at different times. If at decision block 208 it is determined that all results for the order for the patient have not been performed and received, at block 210 the laboratory test result is held until all other results for the order are performed and received by the system.

If at block 208 it is determined that all results for the order have been performed at block 212, the laboratory test results for the order are evaluated against predefined auto-verification rules or criteria. Automatically verifying laboratory test results determines whether the test result is within a predetermined range that is considered to be normal for that type of laboratory test. Information regarding the patient, such as age and sex, may also be taken into account in determining what results are considered to be normal for the type of laboratory test.

At block 214 if it is determined that the laboratory test results passed the predefined auto-verification rules, at block 218 the laboratory test results for the order are automatically verified and at block 220 the results are released for clinical use. If at decision block 214 it is determined that one or more of the laboratory test results for the order do not pass the predefined automatic verification rules, at block 216 all the results for the order are left in a performed status and require manual verification by a clinician or technologist. For example, if one test result of an order fails to satisfy predefined auto-verification rules individually, all of the test results for the order also fail and the results are not automatically verified. In some instances, if a result cannot be manually verified, all of the tests for the order will have to be reperformed. This process prevents some test results of an order from being automatically verified when they should not have because other test results of the order failed to satisfy pre-defined rules.

Figure 3:
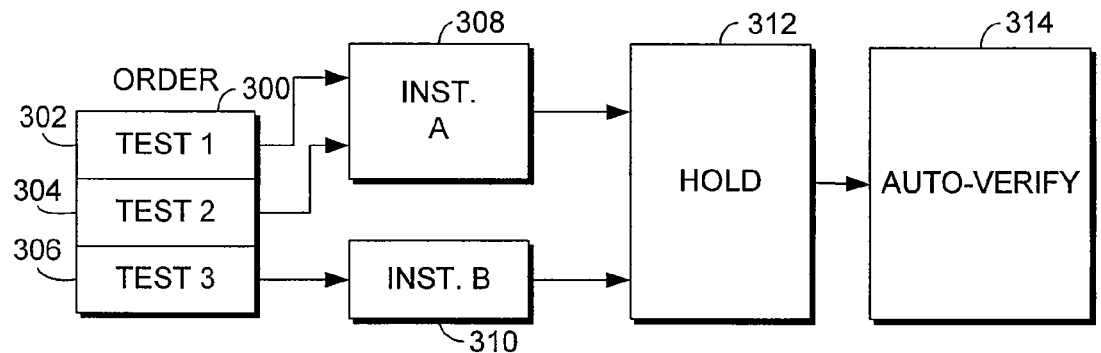
FIG. 3 is a block diagram of automatically verifying a set of laboratory test results for an order performed by multiple instruments in accordance with an embodiment of the present invention.

By way of example, and not by limitation, the following is an example of auto-verification of multiple laboratory test results. A procedure is ordered for a fictitious patient John Smith and a sample of John Smith's blood is drawn. With reference to FIG. 3, the order 300 exemplified by a lipid profile procedure comprises of three instrument-performed detailed tests, Test 1 302, Test 2 304 and Test 3 306, exemplified by a cholesterol test, a triglyceride test, and an HDL test respectively. The detailed tests are performed on two different instruments, Instrument A 308 and Instrument B 310. Instrument A 308 is exemplified by a VITROS 950 instrument and Instrument B 310 by a VITROS 250 instrument.

For example, the cholesterol and triglyceride tests are performed on a VITROS 950 instrument. The HDL test is performed on a VITROS 250 instrument. After each instrument performs the necessary test on the sample received from fictitious patient John Smith, the result is sent as an electronic message and is received at block 202 of FIG. 2. The exemplary message from the VITROS 950 instrument is "VITROS 950: cholesterol=250 mg/dl; triglycerides=150 mg/dl". At block 204 of FIG. 2, it is determined whether any related results or any other results from the order related to the message received from the VITROS 950 instrument are being held. In other words, it is determined whether there are any test results that were part of the lipid profile procedure ordered for fictitious patient John Smith. At block 204, it is determined that no other results for the lipid profile procedure for fictitious patient John Smith are being held and at block 208 it is determined whether all laboratory test results for the lipid profile have been performed. At decision block 208, it is determined that all of the laboratory test results for the lipid profile procedure have not performed and received and there is one test result remaining to be received. The test result still needed is the result for the HDL detail test. As such, at block 210 the laboratory test result message received from the VITROS 950 instrument is placed on hold until all of the other laboratory results for the lipid profile procedure have been performed and received. The hold process is exemplified by block 312 of FIG. 3.

At block 202, another completed laboratory test result message from the VITROS 250 instrument for the HDL detail test for fictitious patient John Smith is received. The exemplary message from the VITROS 250 instrument is "VITROS 250: HDL=<4 mg/dl". At block 204 of FIG. 2, it is determined whether there are any related results to the message received being held. It is determined that another message for the lipid profile procedure for fictitious patient John Smith from the VITROS 950 instrument is being held. At block 206, the related result that is being held is combined with the result from the VITROS 250 instrument.

At block 208, it is determined that all results for the order have been performed and received as the results for the cholesterol test, triglyceride test, and the HDL test for fictitious patient John Smith have all been received from their respective instrument or medical devices. Because all of the test results for the lipid profile procedure for patient John Smith have been received, the results are evaluated against predefined auto-verification rules. It is determined at block 214 that only two of the test results satisfy the predefined auto-verification rules and are within normal ranges for each type of procedure. Thus, since one result has failed auto-verification, at block 218 the entire lipid profile order for patient John Smith including the three results from two different instruments are not auto-verified. The auto-verification process is exemplified by block 314 of FIG. 3.

Figure 4:
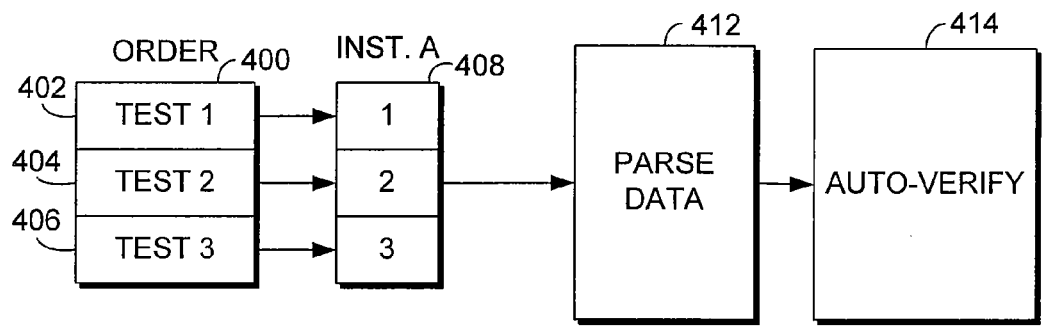
FIG. 4 is a block diagram of automatically verifying multiple laboratory test results from a modular laboratory instrument in accordance with an embodiment of the present invention.

Referring next to FIG. 4, by way of example, and not by limitation, an order 400 for a patient comprising three tests, Test 1 402, Test 2 404 and Test 3, 406 is sent to a modular instrument 408, such as a Modular Analytics SWA (Serum Work Area) produced and sold by Roche Diagnostics. A modular laboratory instrument performs multiple laboratory tests in a different area of the instrument. For example, each of the three Tests 402, 404 and 406 of order 400 is performed in a different area of the modular instrument 408. For example, Test 1 is performed in area 1, Test 2 is performed in area 2 and Test 3 is performed in area 3 of modular instrument 408. The test results for all three of the tests are combined into one data stream received by the auto-verification system. At block 412 the results data stream from the modular instrument 408 is parsed into separate results for each individual test. At block 414, it is determined whether each of the parsed laboratory test results for the order satisfy predefined auto-verification rules. If one test result in an order fails to satisfy predefined auto-verification rules individually, the rules may require that all of the test results for the order fail and are not automatically verified.

The present invention has been described in relation to particular embodiments, which are intended in all respects to illustrative rather than restrictive. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims.

The invention claimed is:

1. A method of holding laboratory test results in a computerized environment, the method comprising:
one or more computing devices executing:
receiving a first laboratory test result for a healthcare order for a patient, wherein the healthcare order comprises multiple laboratory tests that are related to one another;
determining whether all related laboratory test results associated with the laboratory tests for the healthcare order have been received;
upon determining that all related laboratory test results associated with the healthcare order have not been received, holding the first laboratory test result;
after holding the first laboratory test result, determining whether all laboratory test results associated with the laboratory tests for the healthcare order have been received;
after holding the first laboratory test result, determining that any remaining laboratory test results related to the first laboratory test result have been received;
combining the remaining laboratory test results with the first laboratory test result based on the remaining laboratory test results being related to the first laboratory test result; and
upon determining that any remaining laboratory test results related to the first laboratory test result for the healthcare order have been received,
comparing each of the test results to predefined criteria,
based on the comparison, determining that each of the test results is considered to be normal, and
automatically verifying the entire order.

2. The method of claim 1, wherein the results for the healthcare order are received from two or more laboratory instruments.

3. The method of claim 1, further comprising:
receiving the first laboratory test result for a patient from an interfaced laboratory instrument.

4. The method of claim 1, wherein the first laboratory test result is an electronic message.

5. The method of claim 1, further comprising:
receiving a second laboratory test result for the healthcare order for the patient;
determining that all of the test results for the healthcare order have been received;
comparing each of the test results to predefined criteria; and
based on the comparison, automatically validating the healthcare order.

6. A system having a computer to perform a method for suspending processing of laboratory test results in a computerized environment, the system comprising:
the computer configured to execute:
a receiving component for,
(1) receiving a first laboratory test result for a patient, wherein a healthcare order comprises the first laboratory test result and a second laboratory test result that are related to one another, and
(2) receiving the second laboratory test that is related to the first laboratory test after holding the first laboratory test result such that the first laboratory test and the second laboratory test are combined based on the first laboratory test being related to the second laboratory test;
a determining component for determining whether all of the laboratory test results for the healthcare order have been received;
a comparing component for comparing each of the test results for the healthcare order to a predefined criteria;
a suspending component for suspending processing of the first laboratory test result until the second laboratory test result has been received; and
a verifying component for automatically verifying the entire order when all of the test results have been received.

7. The system of claim 6, further comprising a second determining component for determining whether each of the laboratory tests in the healthcare order need to be performed again, wherein the laboratory tests need to be performed again if one or more of the laboratory test results are not within an acceptable range.

8. The system of claim 6, wherein comparing each of the test results for the healthcare order to a predefined criteria further comprises determining that each of the test results is within a predetermined range that is considered to be normal for that type of laboratory test.

9. The system of claim 6, wherein the receiving component receives one or more of the first laboratory test result or the second laboratory test result for a patient from an interfaced laboratory instrument.

10. The system of claim 6, wherein one or more of the first laboratory test result or the second laboratory test result is an electronic message.

11. The system of claim 6, wherein comparing each of the test results for the healthcare order to the predefined criteria further comprises determining whether the test results are within a predetermined range that is considered to be normal for that type of laboratory test.

12. The system of claim 11, wherein the verifying component verifies the entire order when the test results are considered to be normal.

13. A method of holding laboratory test results in a computerized environment, the method comprising:
one or more computing devices executing:
receiving a first laboratory test result for a healthcare order for a patient, wherein the healthcare order comprises the first laboratory test result and a second laboratory test result such that the first laboratory test result and the second laboratory test result are related;
receiving the first laboratory test result before the second laboratory test result has been received;

holding the first laboratory test result until the second laboratory test result has been received; and determining, after holding the first laboratory test result, that the second laboratory test result that is related to the first laboratory test result has been received; and upon receiving the second laboratory test result,
  determining that the first laboratory test result is within a predetermined range that is considered to be normal for that type of laboratory test,
  determining that the second laboratory test result is within the predetermined range that is considered to be normal for that type of laboratory test, and
  automatically verifying the healthcare order.

14. The method of claim 13, further comprising receiving the second laboratory test result for the healthcare order for the patient.

15. The method of claim 13, further comprising:
receiving a third laboratory test result for the healthcare order for the patient; and
determining that the third laboratory test result is not within the predetermined range that is considered to be normal for that type of laboratory test.

16. The method of claim 15, further comprising holding the first laboratory test result and the second laboratory test result.

17. The method of claim 16, wherein manual verification is required by a clinician.

18. The method of claim 15, wherein a third laboratory test associated with the third laboratory test result is performed again.

19. The method of claim 15, wherein the healthcare order is not automatically verified until the third laboratory test result is performed again and it is determined to be within the predetermined range that is considered to be normal for that type of laboratory test.

20. The method of claim 13, wherein the laboratory tests are performed on different instruments.

* * * * *